(12) United States Patent
Zhang et al.

(10) Patent No.: US 11,320,440 B2
(45) Date of Patent: May 3, 2022

(54) APPLICATION OF PDCD4 AS A THERAPEUTIC TARGET FOR ANTIDEPRESSANTS AND/OR ANXIOLYTICS DRUGS

(71) Applicant: SHANDONG UNIVERSITY, Shandong (CN)

(72) Inventors: Lining Zhang, Jinan (CN); Yuan Li, Jinan (CN); Qun Wang, Jinan (CN); Chun Guo, Jinan (CN); Faliang Zhu, Jinan (CN)

(73) Assignee: SHANDONG UNIVERSITY, Shandong (CN)

( * ) Notice: Subject to any disclaimer, the term of this patent is extended or adjusted under 35 U.S.C. 154(b) by 78 days.

(21) Appl. No.: 16/487,934

(22) PCT Filed: Apr. 7, 2017

(86) PCT No.: PCT/CN2017/079746
§ 371 (c)(1),
(2) Date: Oct. 23, 2019

(87) PCT Pub. No.: WO2018/152937
PCT Pub. Date: Aug. 30, 2018

(65) Prior Publication Data
US 2020/0049717 A1    Feb. 13, 2020

(30) Foreign Application Priority Data
Feb. 22, 2017   (CN) .......................... 201710097181.8

(51) Int. Cl.
| | |
|---|---|
| *C12N 15/11* | (2006.01) |
| *G01N 33/68* | (2006.01) |
| *C12N 15/113* | (2010.01) |
| *C12Q 1/6883* | (2018.01) |
| *A61K 45/06* | (2006.01) |
| *C07K 16/24* | (2006.01) |

(52) U.S. Cl.
CPC ..... *G01N 33/6863* (2013.01); *C12N 15/1135* (2013.01); *C12N 15/1138* (2013.01); *C12Q 1/6883* (2013.01); *G01N 33/6896* (2013.01); *A61K 45/06* (2013.01); *C07K 16/24* (2013.01); *C12N 2310/14* (2013.01); *C12Q 2600/158* (2013.01); *G01N 2800/301* (2013.01); *G01N 2800/304* (2013.01)

(58) Field of Classification Search
CPC .. A61K 45/06; A61K 31/713; A61K 31/7088; A61K 31/7115; A61K 31/7125; A61P 25/24
See application file for complete search history.

(56) References Cited

FOREIGN PATENT DOCUMENTS

CN         102719435 A     10/2012

OTHER PUBLICATIONS

Stull and Szoka, Pharmaceutical research 12: 465-483. (Year: 1995).*
Zhao, Lixia; "The Therapuetic Effects and Mechanisms of miR-137 in Rat Model of Post-stroke Depression;" Medicine and Public Health, CNKI Doctoral Dissertations; Shandong University.
Meydan et al.; "MicroRNA Regulators of Anxiety and Metabolic Disorders;" Trends in Molecular Medicine; 2016; pp. 1-15.
Dec. 6, 2017 Search Report issued in International Patent Application No. PCT/CN2017/079746.
Dec. 6, 2017 Written Opinion of the International Searching Authority issued in International Patent Application No. PCT/CN2017/079746.

* cited by examiner

*Primary Examiner* — Ekaterina Poliakova-Georgantas
(74) *Attorney, Agent, or Firm* — Oliff PLC

(57) ABSTRACT

The application of PDCD4 as a drug treatment target for anti-depression and/or anti-anxiety disorders has been proved by experimental research that the increase of PDCD4 is an important factor leading to depression in the process of stress; PDCD4 as a target to inhibit its expression or function can play a good antidepressant role, and has no effect on normal physiological state. Therefore, PDCD4 can be used as a target in the preparation and screening of antidepressant and/or anxiolytic drugs, which has a broad application prospect.

5 Claims, 5 Drawing Sheets
Specification includes a Sequence Listing.

APPLICATION OF PDCD4 AS A THERAPEUTIC TARGET FOR ANTIDEPRESSANTS AND/OR ANXIOLYTICS DRUGS

TECHNICAL FIELD

The disclosure is directed to the field of biomedicine and pharmaceutical technology, which is involved in an application of programmed cell death factor 4 (PDCD4) as a therapeutic target for antidepressant and/or anxiolytic drugs, in particular to an application and an method of PDCD4 as a therapeutic target for screening of antidepressant and/or anxiolytic drugs, and the application of PDCD4 as a therapeutic target for preparing antidepressant and/or anxiolytic drugs.

BACKGROUND

According to the World Health Organization investigation, it is evaluated that by 2020, depression will become the second most common disease in the world. At present, there are 350 million people with depression in the world, and 200,000 people commit suicide due to depression every year. Depression not only reduces the personal life quality, but the increasing incidence and mortality will bring greater burdens to the society and family. Therefore, it is a long-term commitment of scientists to define the pathogenesis and treatment methods of depression.

Depression refers to a type of mood disorder syndrome, which characterized by low mood, thinking slowly and accompanied by psychotic stagnation symptoms such as decreased interest and initiative. Although anxiety and depression are medically divided into two types of mental illness, they are often combined in the clinic and sometimes difficult to identify. Therefore, many scholars suggest that the two should be combined for treatment.

Many types of antidepressant drugs have appeared in the market, including: monoamine oxidase inhibitors, tricyclic drugs and selective serotonin reuptake inhibitors. However, these drugs are generally ubiquitous, with long-lasting effects, strong side effects, and differences in drug sensitivity in the population. Analysis of the reasons may be due to the complex pathogenesis of the disease and the lack of target specificity of the drug. The key to solving such problems lies in finding the exact drug target based on revealing the mechanism of depression.

The onset of depression is mainly due to the interaction between the physiological susceptibility and the external environment. However, genetically, genetic factors account for 30% of depression. A large number of studies have found that certain gene mutations, single nucleotide polymorphisms (SNPs) can increase the susceptibility to disease. Therefore, it has become a method to dig deep into the susceptibility genes associated with depression and to target new antidepressant drugs.

The PDCD4 was first discovered in mice as a tumor suppressor molecule. PDCD4 is known to be highly expressed in multiple organs throughout the mice and humans, such as the spleen, liver, lungs and kidneys, but it has low or not expressed in tumor tissues and cells. In brain tissue, PDCD4 is highly expressed and inhibits the migration and proliferation of glioma, and it has been reported that PDCD4 can be used as a biomarker for glioma, indicating that PDCD4 plays a role in sustaining the normal physiological structure and function of the central nervous system. In addition, the study found that PDCD4 is also a stress-sensitive protein. After stimulation with UV or peroxide, the PDCD4 in the cells are highly expressed. Alcohol exposure to neurons in the brain also leads to an increase in PDCD4 expression. This suggests that PDCD4 may be a stress-sensitive protein. Therefore, the dynamic change of PDCD4 expression in stimulation can be utilized as a basis for drugs, and PDCD4 can be used as a target to inhibit the function of participation, and does not affect normal physiological functions.

SUMMARY

The inventors have previously discovered that PDCD4 is unexpectedly discovered on the basis of tumor and metabolic related diseases. Knockdown PDCD4 expression can completely reverse the chronic stress-induced depression-like and/or anxiety-like symptoms, and can be used as a good target for antidepressants.

For the treatment of depression and/or anxiety, the objective of this disclosure is to provide a new antidepressant and/or anxiolytic drug treatment target, PDCD4, to silence its expression or inhibit its function can be used to depression treatment.

Specifically, the following technical solutions are involved:

The present invention discloses an application of PDCD4 as a target in the preparation of an antidepressant and/or anxiolytic drug which interferes with or inhibits the expression of the PDCD4 gene, or antagonizes the protein function of PDCD4.

The drug affects the expression of the PDCD4 gene or the function of the protein by directly acting on the PDCD4 gene or its protein.

In a preferred embodiment, the interference or inhibition of expression of the PDCD4 gene is achieved by PDCD4 gene knockout.

In a preferred embodiment, the interference or inhibition of expression of the PDCD4 gene is achieved by PDCD4 gene RNA interference or gene silencing, including but not limited to the use of siRNA, shRNA, MicroRNA, and interfering plasmids that produce siRNA, shRNA, and the like.

In a preferred embodiment of the invention, the medicament for inhibiting and antagonizing the protein function of PDCD4 includes but is not limited to, an antibody against PDCD4 protein, a specific antagonist of PDCD4 protein, and the like. Specific antagonists such as PDCD4 proteins include, but are not limited to, mutant proteins or polypeptides of the PDCD4 protein, and expression genes or plasmids of mutant proteins or polypeptides that produce the PDCD4 protein.

The present invention also discloses an antidepressant and/or anxiolytics drug comprising an effective amount of a drug which interferes with or inhibits expression of a PDCD4 gene or a drug which inhibits and antagonizes the protein function of PDCD4, and a pharmaceutically acceptable carrier.

The antidepressant and/or anxiolytics drug is in a liquid dosage form or a solid dosage form.

The liquid dosage form is an injection, a solution, a suspension, an emulsion or an aerosol.

The solid dosage form is a tablet, capsule, pill, powder injection, sustained release preparation or various drug delivery systems.

For the screening of antidepressant and/or anxiolytic drugs, the purpose of the present disclosure is to provide a new drug screening method to select for antidepressant and/or anxiolytic drugs with PDCD4 as a therapeutic target.

Specifically, the present invention relates to the following technical solutions:

The present invention discloses a method of screening for antidepressant and/or anxiolytic drugs comprising the step of screening PDCD4 as a therapeutic target.

PDCD4 is used as a therapeutic target to screen antidepressant and/or anxiolytic drugs, with a decrease or loss of the expression of PDCD4 gene, or an inhibition or deletion of protein function of PDCD4 as a screening index.

In a preferred embodiment, the method of screening for antidepressant and/or anxiolytic drugs includes using a model of depression in an animal, in particular to a chronic resistant stress (CRS) mouse model. PDCD4 mRNA levels and/or protein levels were measured in the hippocampus of CRS mice.

In addition, the objective of the present invention also includes the use of PDCD4 as a target for screening of early warning of depression and/or anxiety and clinical diagnostic reagents.

The diagnostic reagent is used to test the PDCD4 gene expression level or the protein function level of PDCD4.

The research conclusions and beneficial effects of the present invention are as follows:

1. The present invention determines the brain tissue region and cell type of PDCD4 expressed in the central nervous system of mice: First, the distribution of PDCD4 in specific regions of the brain is determined by using the method of dividing the brain region, and then the cell type difference of PDCD4 expression is determined by co-staining with the markers of various types of cells in the brain; indicating that PDCD4 presents in the brain and may be functional.

2. The present invention finds that the expression of PDCD4 in the hippocampus of depressed mice is increased: there are currently three models of depression in animals: social defeat, chronic unpredicted stress (CUS) and chronic resistant stress (CRS), and the present invention used the CRS model simulating the depression behavior caused by stress. The study found that the PDCD4 mRNA and protein in the hippocampus of mice with CRS were significantly increased.

3. The inventors of the present invention found that PDCD4 is also elevated in brain tissue of a person with depression. Through database search, the chip data of brain tissue of existing mental patients were analyzed, and it was found that PDCD4 has a high expression tendency in people with depression and two-way affective disorder.

4. The present invention founds that PDCD4 knockdown can completely reverse the occurrence of stress-induced depression-like and anxiety-like symptoms in depression, indicating that elevation of endogenous PDCD4 can promote the production of depression-like behavior. PDCD4 systemic knockout mice did not have anxiety and depression behavior under normal conditions, but it is interesting to note that PDCD4 whole body knockout mice were modeled by CRS, and by behavioral model tests, it was found that knockout mice did not show stress-induced anxiety and depression-like behavior.

5. The present invention uses small interfering siRNA to silence the expression of PDCD4 in hippocampus, which can completely reverse the anxiety and depression behavior of stress-induced mice, indicating that PDCD4 is a good drug target for antidepressant, inhibiting its expression or its function can achieve antidepressant effects.

6. The present invention demonstrates that elevated PDCD4 is an important factor leading to depression during stress development; PDCD4 as a target inhibits its protein and function, plays a good antidepressant effect, and has no effect on normal physiology.

DETAILED DESCRIPTION

Figure 1:
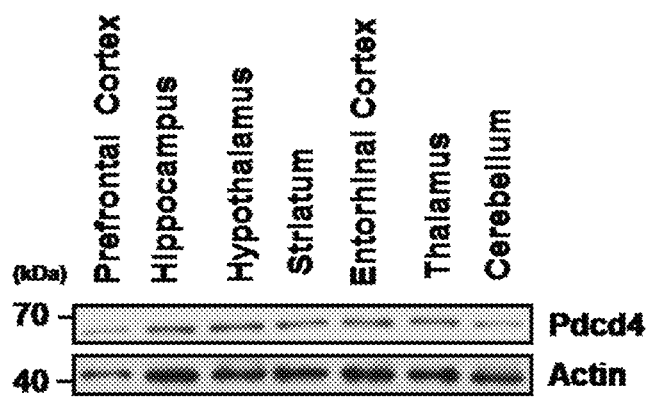
FIG. 1 shows the expression of PDCD4 in various brain regions of mouse brain tissue.

Embodiments of the present disclosure include: PDCD4 is used as a target for the preparation of an antidepressant and/or anxiolytic drug which inhibits the expression of the PDCD4 gene or antagonizes the protein function of PDCD4.

In a preferred embodiment, inhibition of expression of the PDCD4 gene is achieved by PDCD4 gene knockdown, and human PDCD4 gene is mapped, such as chromosome 10q24, and the expressed protein is sequenced to indicate a 469 amino acid composition, including an N-terminal domain, an C-terminal domain and two conserved alpha helix MA-3 domains. The PDCD4 gene knockdown of the present invention includes partial or total knockdown of the PDCD4 gene to achieve loss of PDCD4 gene function.

In another embodiment, inhibition of expression of the PDCD4 gene is achieved by PDCD4 gene interference or gene silencing, which include but is not limited to the use of siRNA, shRNA, MicroRNA, and interfering plasmids that produce siRNA, shRNA, and the like.

For example, CN102719435A discloses an siRNA which inhibits the expression of a PDCD4 gene, and that miR21 inhibits the expression of a PDCD4 gene. They are incorporated in the present invention herein by reference; other siRNAs, shRNAs, microRNAs and interference plasmid that can produce siRNA, shRNA, all of which have been disclosed by the prior art, are also incorporated in the present invention herein by reference.

Regulating PDCD4 gene expression includes two steps: transcription levels and post-transcriptional levels. Regulating of the PDCD4 gene expression at the transcriptional level is achieved mainly by interacting with the regulatory region of the PDCD4 gene, or by methylating 5'CpG island. Therefore, a reagent or a methylated regent that directly interacts with the regulatory region of the PDCD4 gene to reduce PDCD4 gene expression also belongs to the scope of the drug inhibiting the expression of the PDCD4 gene as disclosed in the present invention; regulating of the post-transcriptional level mainly manipulates the expression of PDCD4 negatively by inhibiting mRNA translation or directly degrading mRNA, such as miR-21.

In a preferred embodiment of the invention, the medicament for inhibiting and antagonizing the protein function of PDCD4 includes, but is not limited to, an antibody of PDCD4 protein, a specific antagonist of PDCD4 protein, and the like. Such as, specific antagonists of PDCD4 proteins include, but are not limited to, mutant proteins or polypeptides of the PDCD4 protein, and expression genes or plasmids of mutant proteins or polypeptides that produce the PDCD4 protein.

Embodiments of the present invention also include an antidepressant and/or anxiolytic drug comprising an effective amount of a drug that inhibits expression of a PDCD4 gene or a drug that inhibits and antagonizes the function of a PDCD4 protein, and a pharmaceutically acceptable carrier.

The effective dose refers to a PDCD4 gene expression level or a PDCD4 protein function after administration of a drug has a statistically significant difference from a PDCD4 gene expression amount or a PDCD4 protein function which is not used.

In a preferred embodiment, the antidepressant and/or anxiolytic drug may be in a liquid dosage form or a solid dosage form.

In a more preferred embodiment, the liquid dosage form can be an injection, a solution, a suspension, an emulsion or an aerosol.

In a more preferred embodiment, the solid dosage form is a tablet, capsule, pill, powder injection, sustained release formulation or various microparticle drug delivery systems.

Embodiments of the present disclosure include a method for screening for antidepressant and/or anxiolytic medications comprising the step of screening for PDCD4 as a therapeutic target.

PDCD4 is used as a therapeutic target to screen antidepressant and/or anxiolytic drugs, with a decrease or a deletion of the expression level of PDCD4 gene, or an inhibition or deletion of protein function of PDCD4 as a screening index.

In a preferred embodiment, the screening for antidepressant and/or anxiolytic drugs uses a model of depression in animals, especially a chronic resistant stress (CRS) model to detect the PDCD4 mRNA levels and/or protein levels in the hippocampus brain region of the mice.

In addition, embodiments of the present disclosure also include the use of PDCD4 as a target in screening early warning of depression and/or anxiety and clinical diagnostic reagents.

The diagnostic reagent is used to test the PDCD4 gene expression level or the protein function of PDCD4, including but not limited to conventional PCR primers, fluorescent quantitative PCR primers and fluorescent reagents, PDCD4 antibodies, and the like.

The embodiments of the present invention are only described in the preferred embodiments of the present invention, and are not intended to limit the scope of the present invention. Any modification, equivalent substitution, improvement or the like made within the spirit and principle of the present application shall fall into the protection scope of the present application.

The experimental materials used in the present invention are conventional test materials in the prior art unless otherwise specified.

Example 1: The Expression of PDCD4 in Various Brain Regions of Mouse Brain Tissue Experimental Method:

(1) 6-8 week-old wild-type C57 mice were sacrificed by cervical dislocation and decapitated.

(2) Use the brain trough to divide the brain area. The prefrontal cortex, hippocampus, hypothalamus, striatum, entorhinal cortex, thalamus and cerebellum were obtained and placed in an EP tube and immediately frozen in liquid nitrogen.

(3) The tissue was ground with RIPA, and the supernatant was centrifuged, and boiled at 98° C. to obtain proteins of each brain region.

(4) The expression of PDCD4 protein in each brain region was detected by Rabbit anti-mouse PDCD4 antibody (CST) by Western blot.

(5) Exposure by HRP-ECL color development.

The experimental results are shown in FIG. 1. It is found that PDCD4 is widely distributed in the brain.

Example 2: The Distribution Type of PDCD4 in Brain Cells

Experimental Method:

(1) Wild-type C57 mice were anesthetized with 5% chloral hydrate.

(2) The sternum was cut open, the heart was exposed, and the blood was perfused with saline, and then perfused with 4% paraformaldehyde to the body.

(3) The head was taken from the brain and immersed in 4% paraformaldehyde for 24 hours.

(4) The formaldehyde liquid was changed to a 30% sucrose/PBS solution, and the sugar was precipitated for 3 days until the brain was precipitated at the bottom of the tube.

(5) Fluorescent immunohistochemical staining was performed after slicing by a cryostat.

(6) Labeling PDCD4 with Alexa488 fluorescein secondary antibody (abcam), Alexa594 fluorescein secondary antibody (abcam) labeled neuron Marker NeuN; Alexa488 fluorescein secondary antibody (abcam) labeled Rabbit anti-mouse PDCD4 (Novas) antibody, Alexa594 fluorescence The antibody (abcam) labeled glial Marker GFAP; Alexa 488 fluorescein secondary antibody (abcam) labeled PDCD4, Alexa 594 fluorescein secondary antibody (abcam) microglia Marker Iba1.

Figure 2:
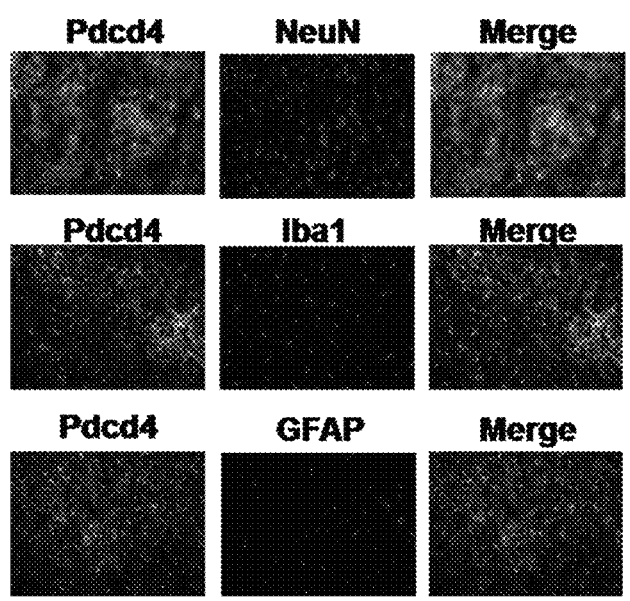
FIG. 2 shows the distribution type of PDCD4 in brain cells.

(7) Observing the co-labeling of PDCD4 and various types of cell markers with confocal microscopy, The experimental results are shown in FIG. 2. It is found that PDCD4 is expressed in neurons and microglia, but is rarely distributed in astrocytes.

Example 3: The Expression of PDCD4 in Mouse Brain Tissue in CRS Model

Experimental Method:

(1) 6-8 week-old wild-type male mice (purchased in Beijing Vital Lihua) were divided into two groups. One group was placed in the restraint stress tube of mice at 9:00 every day for 2 hours for 14 days to expose CRS, n=8; the untreated group for the Naïve group, n=8.

(2) Immediately after the model was established on the 14th day, the mice were decapitated and the brain was obtained, and the hippocampus was obtained and frozen in liquid nitrogen.

(3) One side of hippocampus extracts mRNA using Trizol, reverse transcription into cDNA, and primers of PDCD4 (upstream SEQ ID NO: 1: 5'-AAACAACTCCGT-GATCTTTGTCCA-3; downstream SEQ ID NO: 25'-TCAGGTTTAAGACGGCCTCCA-3') The expression of PDCD4 in each group of mRNA was determined by RT-PCR with (3-actin primer (upstream SEQ ID NO: 3: 5'-CAACTT-GATGTATGAAGGCTTTGGT-3'; downstream SEQ ID NO: 4: 5'-ACTTTTATTGGTCTCAAGTCAGTGTACAG-3').

(4) The other brain tissue was ground with RIPA, protein was collected, and protein expression in each group was detected by Western blot using Rabbit anti-mouse PDCD4 antibody (CST).

Figure 3:
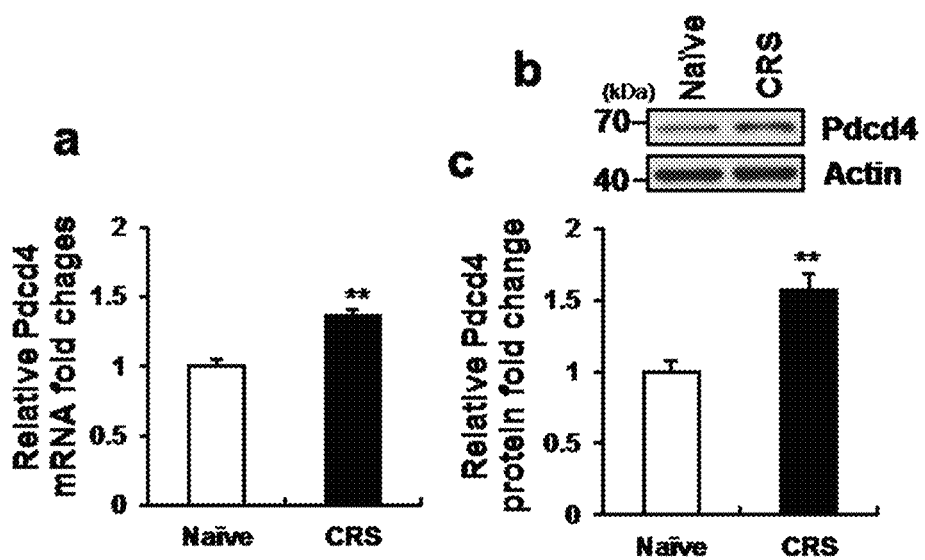
FIG. 3 shows the expression of PDCD4 in mice brain after chronic resistant stress (CRS) administration, wherein a is the PCR result, b is the Western blot picture, c is the statistical result of Western blot protein expression.

PCR analysis, as well as Western blot pictures and statistical results are shown in FIG. 3. The results show that the CRS group has higher PDCD4 mRNA and protein than the Naïve group.

Example 4: Depression-Like Behavior of PDCD4 Knockout Mice after CRS Model

Experimental Method:

(1) Obtaining 6-8 week-old PDCD4 all-knockout male mice (purchased in Jackson Laboratory, Cat. No. 018164) and littermate wild type mice, (2) The two groups of mice were further divided into Naïve and CRS groups, and 8 rats in each group were subjected to CRS modeling.

(3) Depression-like behavioral testing was performed after the fourteenth day. They were tail suspension test, forced swimming test and sucrose preference test.

(4) Tail suspension test: The mice were fixed with a tape to an iron frame about 60 cm high for 6 minutes. The camera recorded the actions of the mice, which were divided into immobile and struggling, and then the ratio of immobility time to total time was calculated.

(5) Forced swimming test: 2 liters of cylinders were filled with 1 liter of water; the mice were placed in water for 6 minutes; the camera recorded the actions of the mice, including immobile and struggling, and calculated the proportion of immobility time to total time.

(6) Sucrose preference test: The mice were kept in a single cage, and two bottles of 1% sucrose water were given for drinking at regular intervals (or two bottles of 1% sucrose water randomly) for 3-5 consecutive days. Test period: 2 days, a bottle of water and a bottle of 1% sucrose water were given to the mice at a fixed time, and the position of the water bottle was exchanged after 24 hours to calculate the drinking amount of sucrose water or the drinking rate of sucrose water (sucrose water/sucrose water+tap water)). If the acclimation period is to drink tap water throughout the day, the amount of water consumed during the test period is also the amount of drinking throughout the day.

Figure 4:
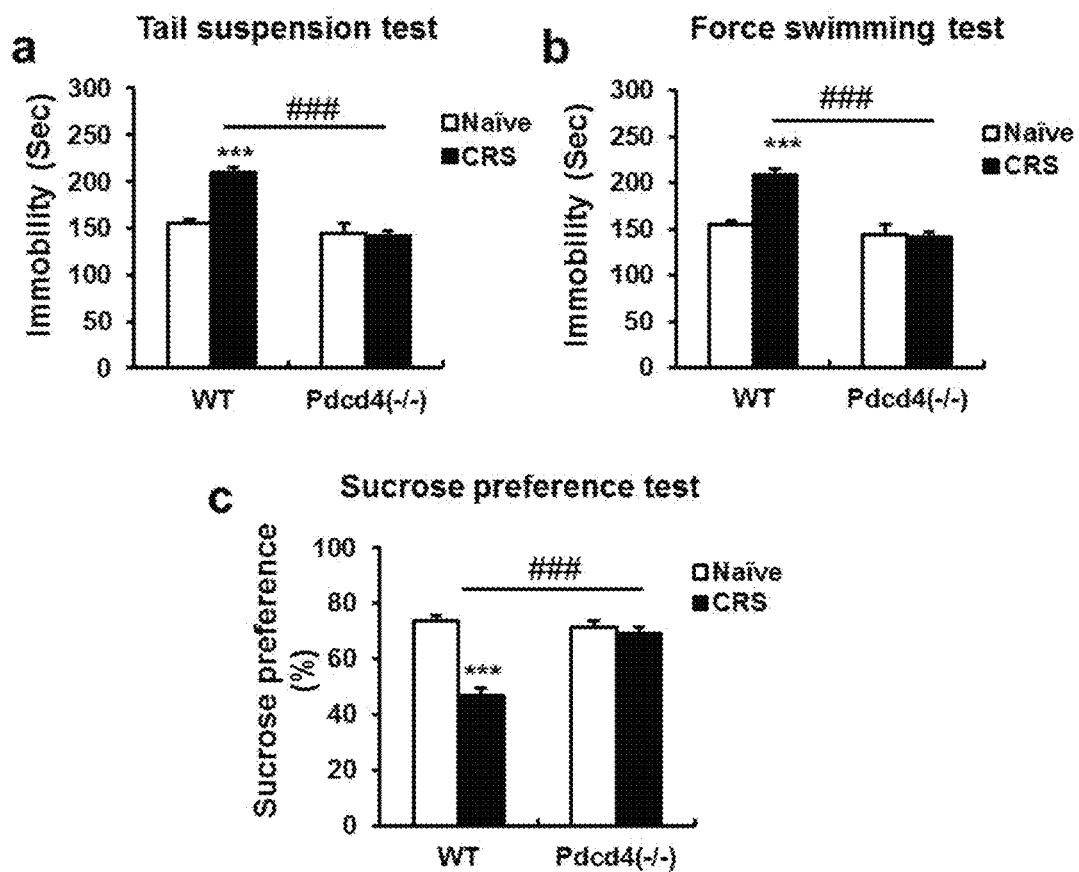
FIG. 4 shows depression-like behavioral of PDCD4 knockout mice after CRS exposure, wherein a is the result of the tail suspension test, b is the result of the forced swimming test, and c is the result of the sucrose preference test.

Analysis of behavioral test results is shown in FIG. 4. FIG. 4a and FIG. 4b show tail suspension test and forced swimming test for behavioral test. The immobility time is proportional to the degree of behavioral despair. It is not difficult to find that wild-type mice show obviously increased immobility ratio after CRS modeling. But CRS modeling in PDCD4 knockout mice did not increase the immobility time of the mice. FIG. 4c sucrose preference test is used for testing the pleasure in mice, and the lower proportion of sucrose water in total drinking water indicates the mice lost pleasure. Statistics of the index show that wild-type mice show significant sucrose-preferential reduction after CRS modeling, but CRS modeling in PDCD4 knockout mice do not show the lack of pleasure in wild-type mice. The results show that in wild-type mice, CRS can cause depression-like behavior, PDCD4 knockout does not affect the depression-like mood of mice, and exhibits anti-depressant-like behavior after CRS modeling of systemic knockout.

Example 5: Anxiety-Like Behavioral Behavior of PDCD4 Knockout Mice after CRS Model Experimental Method:

(1) 6-8 week-old PDCD4 all-knockout male mice (purchased in Jackson Laboratory, catalog No. 018164) and littermate wild type mice were obtained, and the two groups of mice were further divided into Naïve and CRS groups, 8 in each group. Perform CRS modeling, perform open field test, and test the anxiety-like behavior in the elevated cross maze.

(2) Open field test: The mice were placed in a 60 cm×60 cm open field, and the camera recorded the movement of the mice. The 20 cm×20 cm area in the middle of the market is defined as the central area, and the software obtains the mouse action route, analyzing the total distance of the exercise and the proportion of time spent in the central area.

(3) Elevated plus maze: The elevated cross maze consists of a pair of open arms and a pair of closed arms. The mice were placed in an elevated plus maze and the software was used to analyze the trajectories of the mice, and the time of the mice in the open and closed arms, the number of access to the open and closed arms were calculated.

Figure 5:
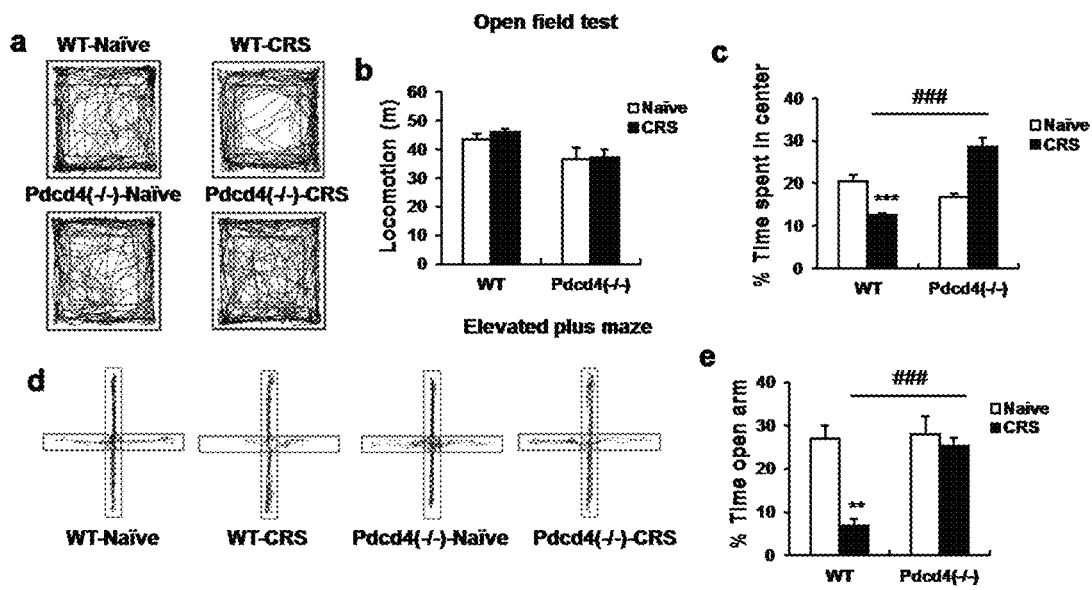
FIG. 5 shows anxiety-like behavioral expression of PDCD4 knockout mice after CRS exposure, wherein a is the trajectory map of the mice in the open field test, b is the exercise ability of the mice in the open field test, c is the time of exploration in the central area of the open field test, d is the trajectory of the elevated plus maze, and e is the exploration time of the elevated plus maze.

The behavioral statistics of mice are shown in FIG. 5. The FIGS. 5a and 5c use the open field test to detect the motor ability and anxiety of the mice. The FIG. 5b shows that there is no change in the immobility of wild-type mice and PDCD4 mice. FIG. 5c shows that the wild-type mice show a decrease in the exploration time in the central region of the open field after CRS modeling, but do not show this phenomenon after the CRS model of PDCD4 knockout mice. The results show that CRS in wild-type mice can cause anxiety-like behavior, PDCD4 knockout does not affect the anxiety of mice, and PDCD4 conventional knockout shows anti-anxiety behavior after CRS modeling.

Example 6: Located Injection of Lentivirus Packaged with PDCD4siRNA into Hippocampus and the Detection of Depression-Like Behavior in Mice Experimental Method:

(1) Packing siPDCD4 and GFP lentivirus (obtained by Shanghai JiKai Gene Chemical Technology Co., Ltd.), titer $7 \times 10^7$.

(2) Wild-type C57 mice were anesthetized with chloral hydrate, and the mice were fixed on a brain stereotaxic instrument to expose the skull. Coordinates: before and after −2.03, left and right ±2.4, drilling holes, micro syringe suction (1.5 μl per Side), fixed vertically on the locator, with a needle depth of 1.87, injected into the hippocampus region of the mouse at 0.1 μl/min.

(3) After 7 days of recovery, the mice were subjected to CRS modeling.

(4) Depression-like behaviors were detected 14 days after modeling, which were tail suspension test, forced swimming test and sucrose water preference test. The experimental method was the same as that in the fourth example.

Figure 6:
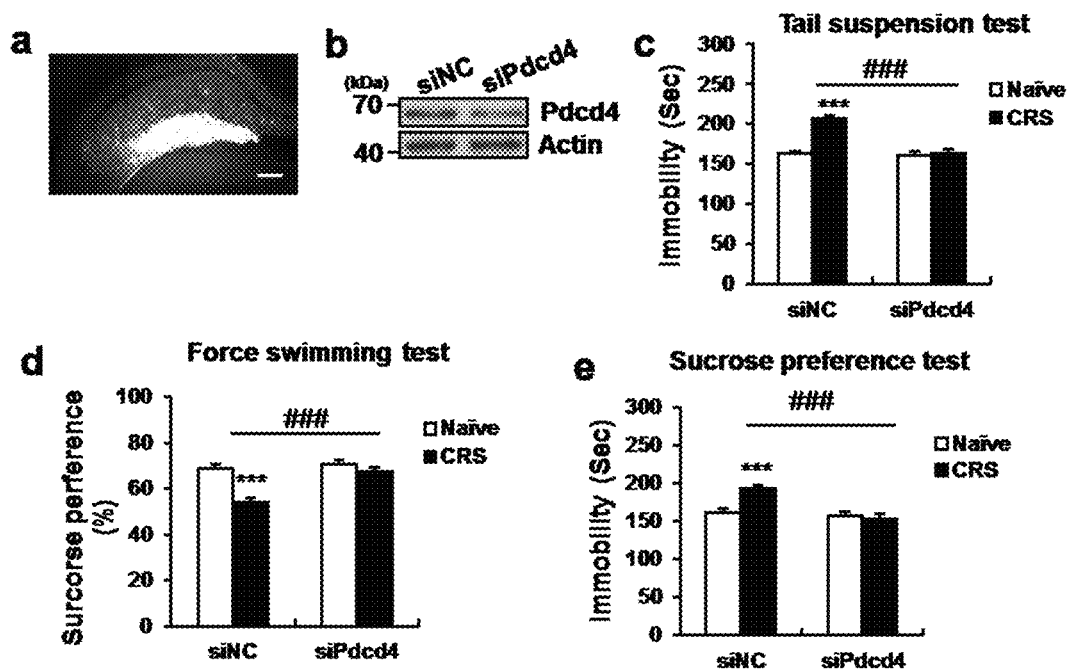
FIG. 6 shows the depression-like behavioral expression in mice whose hippocampal region was injected into the lentivirus packaged with PDCD4 siRNA; herein a is a virus diffusion map, b is interference efficiency test in vivo. c is the result of the tail suspension test, d is the result of forced swimming test, e is the result of sucrose preference test.

(5) Analysis of behavioral test results is shown in FIG. 6. FIG. 6c-6d show the tail suspension test and forced swimming test for behavioral despair. The immobility time is directly proportional to the degree of behavioral despair. It is not difficult to find a significant increase immobility ratio of the mice injected lentiviral GFP after CRS modeling, but the immobility time of the mice injected lentivirus siPDCD4 does not increase after CRS modeling. FIG. 6e sucrose preference test shows that mice lacked pleasure and the lower proportion of sucrose water in total drinking water indicates the mice lost pleasure. Statistical results shows that the mice injected with lentivirus GFP show a significant decrease in sugar preference after CRS modeling, but there is no lack of pleasure in the mice injected with lentivirus siPDCD4 after CRS modeling as in wild-type mice. The results show that CRS in mice injected with GFP virus could cause depression-like behavior, and siPDCD4 injection does not affect the depression-like behavior of mice, but mice injected with siPDCD4 show antidepressant-like behavior after CRS modeling.

(6) Immunofluorescence histochemistry reflect the spread of the virus and Western blot reflects the effect of PDCD4 in vivo, as shown in FIGS. 6a and 6b.

Example 7: Located Injection of Lentivirus Packaged with PDCD4siRNA into Hippocampus and Detection of Anxiety-Like Behavior in Mice Experimental Method:

(1) Anxiety-like behavior test, open field test, and elevated plus maze were used to detect anxiety-like behavior in mice injected with GFP virus and siPDCD4 virus. The experimental method was the same as in example 5.

Figure 7:
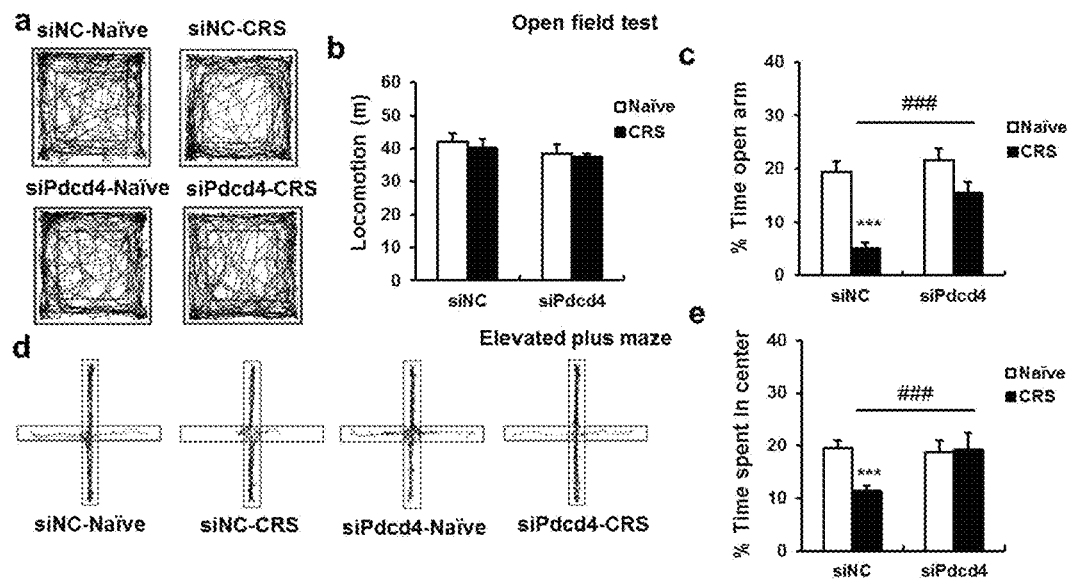
FIG. 7 shows anxiety-like behavioral expression in mice whose hippocampal region was injected into the lentivirus of PDCD4 siRNA, wherein a is the trajectory map of the mice in the open field test, b is the exercise ability of the mice in the open field test, c is the exploration time in the central area of the open field test, d is the trajectory of the elevated cross maze mouse, and e is the exploration time of the elevated plus maze.

(2) Analysis of behavioral test results is shown in FIG. 7. a-c show the open field test to detect locomotion and anxiety behavior in mice. FIG. 7b shows that there was no change in immobility of mice injected with GFP and siPDCD4. FIG. 7c shows that, after the CRS modeling, the exploration time is reduced in the central area of the open field, but this phenomenon is not observed in the mice injected with siPDCD4 after CRS modeling. The results show that in mice injected with GFP virus CRS could cause anxiety-like behavior, siPDCD4 injection does not affect the anxiety of mice, and the mice injected with siPDCD4 show anxiolytic behavior after CRS modeling.

Example 8: Screening of PDCD4 Expression in Brain Tissue of Patients with Mental Disorders Experimental Method:

(1) The results of RNA microarray performed by researchers on brain tissue of mentally ill people were retrieved from the public GEO website (database file number: GDS3345/39510_r_at).

(2) Using the absolute value of expression presented by the chip, the mRNA expression of PDCD4 in psychiatric diseases was analyzed by SPSS software statistical One-way ANOVA.

Figure 8:
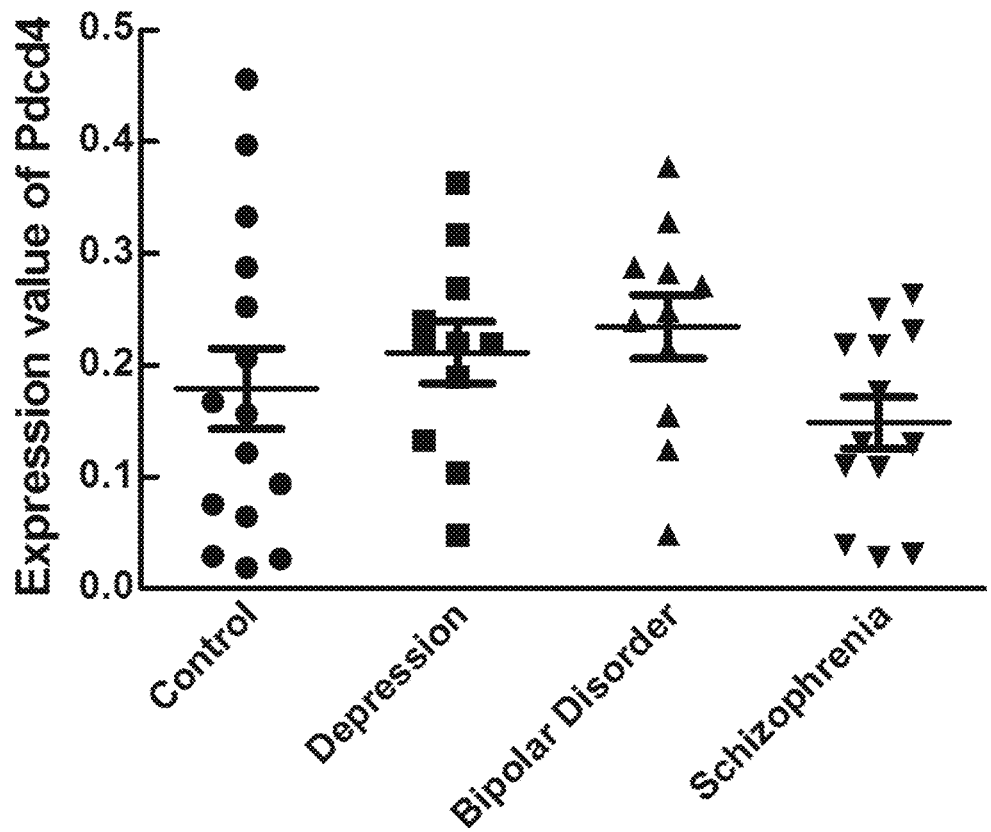
FIG. 8 shows the screened microarray data of the expression of PDCD4 in brain tissue of patients with mental disorders.

(3) Analysis of the results is shown in FIG. 8. PDCD4 has a high expression trend in the brains of patients with depression and two-way mental disorders, but there is no change in the schizophrenic population.

Example 9: The Interference Effect of PDCD4 siRNA on Human Cells

Experimental Method:

(1) Human siRNA was designed for PDCD4 (sequence SEQ ID NO: 5: GAGAUGGAAUUUUAUGUAAUU), Shanghai JIMA Synthetic siRNA powder.

(2) HEK293 cells highly expressed PDCD4 and were seeded in a six-well plate at a density of $5 \times 10^5$.

(3) After 24 hours, 1 μl of siRNA or negative control (synthesis of Shanghai Gemma, sequence: UUCUCCGAACGUGUCACGUTT) was added to the cells with 2 μl of lipo2000, and after 4-6 hours, the cells were replaced with cell culture medium. After 24 hours, RIPA was used to collect cellular proteins.

(4) Detection of PDCD4 expression by Western blot.

Figure 9:
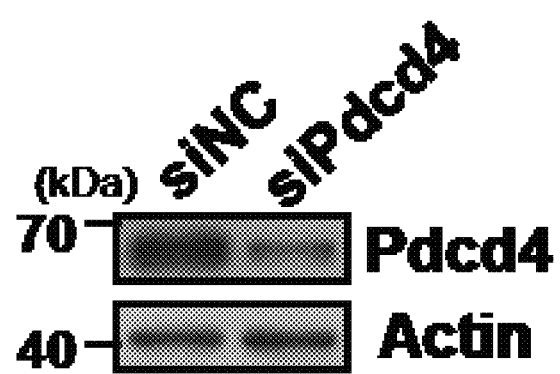
FIG. 9 shows the interference effect of PDCD4 siRNA on human cells.

(5) As a result, it is found that, as shown in FIG. 9, the amount of PDCD4 is much lower than that of the siPDCD4 group compared with NC.

---

The invention claimed is:

1. A method for treating stress-induced depression in a person in need thereof, the method comprising:
   administering, to the person, an effective amount of an antidepressant drug which interferes with or inhibits the expression of a programmed cell death factor 4 (PDCD4) gene,
   wherein the drug includes siRNA having the nucleotide sequence according to SEQ ID NO: 5.

2. An antidepressant medicament comprising an effective amount of a drug which interferes with or inhibits the expression of the PDCD4 gene
   wherein the drug includes siRNA having the nucleotide sequence according to SEQ ID NO: 5.

3. The medicament according to claim 2, in a liquid dosage form selected from the group consisting of an injection, a solution, a suspension, an emulsion, and an aerosol.

4. A method for decreasing expression of a programmed cell death factor 4 (PDCD4) gene in a person in need thereof, the method comprising:
   administering, to the person, an effective amount of a drug which interferes with or inhibits the expression of a programmed cell death factor 4 (PDCD4) gene,
   wherein the drug includes siRNA having the nucleotide sequence according to SEQ ID NO: 5.

5. The medicament according to claim 2, in a solid dosage form selected from the group consisting of a tablet, a capsule, a pill, a powder injection, a sustained release formulation, and various microparticle delivery systems.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
aaacaactcc gtgatctttg tcca                                          24
```

```
<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tcaggtttaa gacggcctcc a                                          21

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
caacttgatg tatgaaggct ttggt                                      25

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
acttttattg gtctcaagtc agtgtacag                                  29

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gagatggaat tttatgtaat t                                          21
```